(12) United States Patent
Fukui et al.

(10) Patent No.: US 7,932,028 B2
(45) Date of Patent: Apr. 26, 2011

(54) PROBE SET, PROBE IMMOBILIZED CARRIER AND METHOD FOR DETECTING MICROORGANISMS

(75) Inventors: Toshifumi Fukui, Yokohama (JP); Nobuhiro Tomatsu, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/602,279

(22) Filed: Nov. 21, 2006

(65) Prior Publication Data

US 2007/0134702 A1  Jun. 14, 2007

(30) Foreign Application Priority Data

Dec. 9, 2005  (JP) ................................ 2005-355977

(51) Int. Cl.
 C12Q 1/68 (2006.01)
 C12P 19/34 (2006.01)
 C07H 21/02 (2006.01)
 C07H 21/04 (2006.01)

(52) U.S. Cl. ......... 435/6; 435/91.2; 536/23.1; 536/23.7; 536/24.2; 536/24.32; 536/24.33

(58) Field of Classification Search .................. None
 See application file for complete search history.

(56) References Cited

U.S. PATENT DOCUMENTS

| | | | |
|---|---|---|---|
| 5,464,743 A | 11/1995 | Weisburg et al. | |
| 5,512,446 A | 4/1996 | Miyazaki et al. | 435/7.2 |
| 5,580,971 A | 12/1996 | Mitsuhashi | 536/24.32 |
| 5,700,647 A | 12/1997 | Miyazaki et al. | 435/6 |
| 5,722,464 A | 3/1998 | Truyen et al. | |
| 5,846,730 A | 12/1998 | Miyazaki et al. | 435/6 |
| 5,958,693 A | 9/1999 | Sandhu et al. | |
| 6,046,006 A | 4/2000 | Einsele et al. | 435/6 |
| 6,150,517 A | 11/2000 | Hogan et al. | |
| 6,605,439 B2 | 8/2003 | Einsele | 435/6 |
| 6,773,882 B2 * | 8/2004 | Hogan et al. | 435/6 |
| 2004/0002592 A1 | 1/2004 | Einsele et al. | |
| 2004/0241643 A1 | 12/2004 | Yamamoto et al. | 435/5 |

FOREIGN PATENT DOCUMENTS

| | | |
|---|---|---|
| DE | 195 30 332 | 2/1997 |
| DE | 195 30 333 | 2/1997 |
| DE | 196 35 347 | 12/1997 |
| EP | 0 422 869 | 4/1991 |
| EP | 0 422 873 | 4/1991 |
| JP | 8-89254 | 4/1996 |
| JP | 2002223766 A * | 8/2002 |
| JP | 2004-313181 | 11/2004 |

OTHER PUBLICATIONS

NCBI Database, National Library of Medicine, NIH (Bethesda, MD, USA), GenBank Accession No. AF114470, Mar. 25, 1999.*
NCBI Database, National Library of Medicine, NIH (Bethesda, MD, USA) GenBank Accession No. AJ842962 (Dec. 1, 2004.*
Hermann Einsele, et al., "Detection and Identification of Fungal Pathogens in Blood by Using Molecular Probes", Journal of Clinical Microbiology, vol. 35, No. 6, Jun. 1997, pp. 1353-1360.
R. Kappe, et al., "Molecular probes for the detection of pathogenic fungi in the presence of human tissue", J. Med. Microbiol., vol. 47, 1998, pp. 811-820.
R. Kappe, et al., "Universal fungus-specific primer systems and group-specific hybridization oligonucleotides for 18S rDNA", Mycoses, vol. 39, 1996, pp. 25-30.
Dirk M. Leinberger, et al., "Development of a DNA Microarray for Detection and Identification of Fungal Pathogens Involved in Invasive Mycoses", Journal of Clinical Microbiology, vol. 43, No. 10, Oct. 2005, pp. 4943-4953.
N. Vanittanakom, et al., "Specific identification of *Penicillium marneffei* by a polymerase chain reaction/hybridization technique", Medical Mycology, vol. 36, 1998, pp. 169-175.
Myra N. Widjojoatmodjo, et al., "Nucleic acid sequence-based amplification (NASBA) detection of medically important *Candida* species", Journal of Microbiological Methods, vol. 38, 1999, pp. 81-90.
Search Report dated Dec. 21, 2007 in European Application No. 06024448.0.
Official Action dated Feb. 15, 2008 in Chinese Application No. 200610164184.0.

* cited by examiner

*Primary Examiner* — Carla Myers
(74) *Attorney, Agent, or Firm* — Fitzpatrick, Cella, Harper & Scinto

(57) ABSTRACT

A probe and a primer capable of collectively detecting microorganisms of the same species while differentiating microorganisms of other species with an object of classification by species of fungus. An oligonucleotide probe for detecting an infectious etiologic microorganism gene includes at least one base sequence selected from the base sequences belonging to one group of the following first to ninth groups. The base sequence groups of first to ninth groups are: first group (SEQ ID NOS:1 to 5); second group (SEQ ID NOS:6 to 10); third group (SEQ ID NOS:11 to 15); fourth group (SEQ ID NOS: 16 to 21); fifth group (SEQ ID NOS:22 to 26); sixth group (SEQ ID NOS:27 to 31); seventh group (SEQ ID NOS:32 to 36); eighth group (SEQ ID NOS:37 to 41); and ninth group (SEQ ID NOS:42 to 46).

10 Claims, 1 Drawing Sheet

FIG. 1

| | |
|---|---|
| 95°C | 10 min. |
| 92°C | 45 sec. |
| 67°C | 45 sec. |
| 72°C | 45 sec. |
| 72°C | 10 min. |

92°C–72°C: CYCLES

FIG. 2

| | |
|---|---|
| 95°C | 10 min. |
| 92°C | 45 sec. |
| 65°C | 45 sec. |
| 72°C | 45 sec. |
| 72°C | 10 min. |

92°C–72°C: CYCLES

PROBE SET, PROBE IMMOBILIZED CARRIER AND METHOD FOR DETECTING MICROORGANISMS

BACKGROUND OF THE INVENTION

1. Field of the Invention

The present invention relates to a probe set derived from an infectious etiologic microorganism, which is useful for detection and identification of a causative microorganism of an infectious disease, and a probe immobilized carrier having the probe immobilized thereon. The present invention further relates to a method for detecting an infectious etiologic microorganism gene using the probe set. The present invention furthermore relates to a primer set for effectively amplifying in advance nucleic acids in a specimen used for the detection method.

2. Description of the Related Art

Reagents and methods for detecting rapidly and reliably a pathogenic fungus in a specimen have been conventionally suggested. For example, Japanese Patent Application Laid-Open No. H08-089254 discloses an oligonucleotide comprising a specific base sequence, usable as a probe and a primer, for detecting an etiologic microorganism of candidiasis and aspergillosis, and a method for detecting a target microorganism using the same. Further, the same patent document discloses a primer set for amplifying a plurality of target microorganisms simultaneously by PCR. Moreover, it discloses that, using the primer set, a plurality of target fungi in the specimen are amplified by PCR, and then a sequence part specific to each fungus is detected by hybridization assay using a probe specific to each fungus to identify the species of fungus in the specimen.

On the other hand, as a method for simultaneously detecting oligonucleotides comprising a plurality of different base sequences, known is a method using a probe array wherein a probe having a sequence complementary to each of the base sequence is distantly immobilized on a solid phase (Japanese Patent Application Laid-Open No. 2004-313181).

SUMMARY OF THE INVENTION

However, it is never easy to set a probe capable of simultaneously detecting a plurality of fungi using a probe array, etc. while moderating influence (cross-contamination) to specificity and presence information among each other. In practice, there is no other choice to set a probe individually to a plurality of target fungi to be detected simultaneously. Under these circumstances, the present inventors have studied a probe that can be preferably used to simultaneously detect the following nine fungi while lowering the level of cross-contamination.

1) *Candida albicans*
2) *Candida glabrata*
3) *Candida guilliermondii*
4) *Candida krusei*
5) *Candida parapsilosis*
6) *Cryptococcus neoformans*
7) *Trichosporon beigelii*
8) *Aspergillus fumigatus*
9) *Aspergillus niger*

A first object of the present invention is to provide a probe set capable of simultaneously and more reliably identifying at least two fungi selected from the above nine fungi. Further, another object of the present invention is to provide a probe-immobilized carrier that can be used for simultaneously and more reliably identifying at least two fungi selected from the above nine fungi. Furthermore, another object of the present invention is to provide a primer set capable of amplifying the above nine fungi selectively and to a detectable level by an oligonucleotide forming the above probe set. Moreover, another object of the present invention is to provide a kit for infectious etiologic microorganism detection capable of detecting the above nine fungi with more rapid and accuracy when at least two of fungi selected from the above nine fungi is contained in a specimen.

A probe set of the present invention for detecting an infectious etiologic microorganism, (1) comprising a first probe belonging to a group selected from the following first to ninth groups, and a second probe belonging to a group that is selected from the following first to ninth groups and different from the group of the first probe; or (2) comprising a third probe having a base sequence complementary to the first probe, and a fourth probe having a base sequence complementary to the second probe.

First Group:

(1) a probe having a base sequence comprising acgatacagggccctttttgggt;        (SEQ ID NO: 1)

(2) a probe having a base sequence comprising atctttttcgatgcgtactggaccag;     (SEQ ID NO: 2)

(3) a probe having a base sequence comprising gccatttatggcgaaccaggactt;       (SEQ ID NO: 3)

(4) a probe having a base sequence comprising aggacgttatggttctattgtgttggtt;   (SEQ ID NO: 4)

(5) a probe having a base sequence comprising ggactatcgactccaagtcgatgga       (SEQ ID NO: 5)

Second Group:

(1) a probe having a base sequence comprising cggtccgattttttcgtgtactgga;      (SEQ ID NO: 6)

(2) a probe having a base sequence comprising aaccccaagtccttgtggcttg;         (SEQ ID NO: 7)

(3) a probe having a base sequence comprising tggaataatggaataggacgtttggttct;  (SEQ ID NO: 8)

(4) a probe having a base sequence comprising ttttagtgacccactcggcacct;        (SEQ ID NO: 9)

(5) a probe having a base sequence comprising gctagcatttgctggttgtccact        (SEQ ID NO: 10)

Third Group:
(1) a probe having a base sequence comprising gatacagggccctttcgggtct;    (SEQ ID NO: 11)

(2) a probe having a base sequence comprising ttttggcgagtactggacccaac;    (SEQ ID NO: 12)

(3) a probe having a base sequence comprising ctaaccattcgccttgtggtgtt;    (SEQ ID NO: 13)

(4) a probe having a base sequence comprising atcgggtgttgttcttttttgacgc;    (SEQ ID NO: 14)

(5) a probe having a base sequence comprising aaatagtgctgctagcttttgctggt    (SEQ ID NO: 15)

Fourth Group:
(1) a probe having a base sequence comprising atataacgatacagggcctttggtcttg;    (SEQ ID NO: 16)

(2) a probe having a base sequence comprising ggcggacggtctacctatggtaa;    (SEQ ID NO: 17)

(3) a probe having a base sequence comprising accaggacgattactttgaggaaattaga;    (SEQ ID NO: 18)

(4) a probe having a base sequence comprising ggtggtgctactttgcccactc;    (SEQ ID NO: 19)

(5) a probe having a base sequence comprising agacttctcttgatcttacgggtggt;    (SEQ ID NO: 20)

and
(6) a probe having a base sequence comprising aaatagggctgcgagcatctgc    (SEQ ID NO: 21)

Fifth Group:
(1) a probe having a base sequence comprising gccggtccatctttttgatgcgta;    (SEQ ID NO: 22)

(2) a probe having a base sequence comprising tctggctagccttttggcgaac;    (SEQ ID NO: 23)

(3) a probe having a base sequence comprising tcagtattcagtagtcagaggcgaaattc;    (SEQ ID NO: 24)

(4) a probe having a base sequence comprising tgttgttcttttattgacgcaatcggc;    (SEQ ID NO: 25)

and
(5) a probe having a base sequence comprising tgctgctagcatttgctggtatagtc    (SEQ ID NO: 26)

Sixth Group:
(1) a probe having a base sequence comprising acaatacagggctcttttgggcc;    (SEQ ID NO: 27)

(2) a probe having a base sequence comprising ctggtggtcctgtatgctcttactg;    (SEQ ID NO: 28)

(3) a probe having a base sequence comprising ttgacggaagaccaacaactgcg;    (SEQ ID NO: 29)

(4) a probe having a base sequence comprising gatcggcccacgtcaatctctg;    (SEQ ID NO: 30)

and
(5) a probe having a base sequence comprising cggcgtctagtcgacggaagtt    (SEQ ID NO: 31)

Seventh Group:
(1) a probe having a base sequence comprising gaggaacggtctgccttacggta;    (SEQ ID NO: 32)

(2) a probe having a base sequence comprising ttcattgagtgtgcggtggaacc;    (SEQ ID NO: 33)

(3) a probe having a base sequence comprising cttagatttacggaagactaacaactgcg;    (SEQ ID NO: 34)

(4) a probe having a base sequence comprising tcggtccacgttattttctgactgga;    (SEQ ID NO: 35)

and
(5) a probe having a base sequence comprising ggactaacagcgtttagctgttggaa    (SEQ ID NO: 36)

Eighth Group:
(1) a probe having a base sequence comprising ttctggggaacctcatggcctt;    (SEQ ID NO: 37)

(2) a probe having a base sequence comprising atagggatagtcgggggcgtca;    (SEQ ID NO: 38)

(3) a probe having a base sequence comprising aaagcattcgccaaggatgttttcattaa;    (SEQ ID NO: 39)

(4) a probe having a base sequence comprising cggtgtttctatgatgacccgctc;    (SEQ ID NO: 40)

and
(5) a probe having a base sequence comprising cttcttaggggactatcggctca    (SEQ ID NO: 41)

Ninth Group:
(1) a probe having a base sequence comprising ggggctcttttgggtctcgtaatt;    (SEQ ID NO: 42)

(2) a probe having a base sequence comprising ctggggaatctcatggccttcac;    (SEQ ID NO: 43)

(3) a probe having a base sequence comprising ggatagtcggggcgtcagtatt;    (SEQ ID NO: 44)

(4) a probe having a base sequence comprising gtgtttctattatgacccgttcggca;    (SEQ ID NO: 45)

and
(5) a probe having a base sequence comprising agacctcggcccttaaatagccc    (SEQ ID NO: 46)

A probe-immobilized carrier of the present invention is characterized in that a plurality of probes constituting the above probe set are disposed on a solid phase of the carrier distantly from each other.

A method of the present invention for detecting an infectious etiologic microorganism gene in a specimen using a probe-immobilized carrier, comprises the steps of:
(i) reacting the above probe-immobilized carrier with the specimen; and
(ii) detecting the reaction strength of an oligonucleotide that has been reacted with a nucleic acid in the specimen.

A primer set of the present invention is for amplifying a nucleic acid in a specimen in advance in detecting an infectious etiologic microorganism using the probe-immobilized carrier with the above structure. The primer set has a primer comprising a base sequence of gccctatcaactttcgatggtaggatag (SEQ ID NO:47) and at least one of the following two kinds of primers,
(1) a primer comprising aatgctctatccccagcacgac (SEQ ID NO:48); and
(2) a primer comprising tcggcaccttacgagaaatcaaagt (SEQ ID NO: 49).

According to the present invention, if a specimen has combined infection of at least two microorganisms selected from the above nine causative microorganisms of infectious diseases, the two or more microorganisms can be simultaneously detected from the specimen. Therefore, the determination on whether or not a specimen is infected with a plurality of fungi and, in case of combined infection, the identification of causative microorganisms can be conducted rapidly and accurately. Further, in examining a suspected specimen with combined infection by the probe set of the present invention, the above nine infectious etiologic microorganisms can be selectively amplified without losing reaction specificities with the probes constituting the probe set, by using the primer set of the present invention. Therefore, the examination of a specimen by the probe set or probe-immobilized carrier of the present invention can be carried out with more prompt and accuracy by using the primer set of the present invention for amplification of the specimen.

Further features of the present invention will become apparent from the following description of exemplary embodiments with reference to the attached drawings.

BRIEF DESCRIPTION OF THE DRAWINGS

FIG. 1 is a view showing a PCR condition.
FIG. 2 is a view showing a PCR condition.

DESCRIPTION OF THE EMBODIMENTS

Hereafter, preferred embodiments of the present invention will be described in detail.

In the following embodiments, sets of oligonucleotide probes (hereinafter simply referred to as probes) for identifying infectious etiologic microorganisms are shown. Using this probe set, one of the following nine fungi causing inflammation by their infection or plural kinds thereof can be detected.
1) *Candida albicans*
2) *Candida glabrata*
3) *Candida guilliermondii*
4) *Candida krusei*
5) *Candida parapsilosis*
6) *Cryptococcus neoformans*
7) *Trichosporon beigelii*
8) *Aspergillus fumigatus*
9) *Aspergillus niger*

Namely, disclosed is a nucleic acid probe set for detecting 18S rRNA gene sequence among the genes of the above nine kinds of infectious etiologic microorganisms without excess and deficiency.

According to the present embodiment, probes for the probe set that reacts itself with a specimen (a solution for examination) containing a gene itself of an infectious etiologic microorganism or a nucleic acid having a base sequence specific to the gene of the microorganism, can be selected from each of at least two groups of the following first to ninth groups.

First Group:
(1) a probe having a base sequence comprising acgatacagggccctttggggt;    (SEQ ID NO: 1)

(2) a probe having a base sequence comprising atcttttcgatgcgtactggaccag;    (SEQ ID NO: 2)

(3) a probe having a base sequence comprising gccatttatggcgaaccaggactt;    (SEQ ID NO: 3)

(4) a probe having a base sequence comprising aggacgttatggttctattgtgttggtt;    (SEQ ID NO: 4)

and
(5) a probe having a base sequence comprising ggactatcgactccaagtcgatgga        (SEQ ID NO: 5)

Second Group:
(1) a probe having a base sequence comprising cggtccgattttttcgtgtactgga;       (SEQ ID NO: 6)

(2) a probe having a base sequence comprising aaccccaagtccttgtggcttg;          (SEQ ID NO: 7)

(3) a probe having a base sequence comprising tggaataatg-gaataggacgtttggttct (SEQ ID NO:8);
(4) a probe having a base sequence comprising ttttagtgacccactcggcacct;         (SEQ ID NO: 9)

and
(5) a probe having a base sequence comprising gctagcatttgctggttgtccact         (SEQ ID NO: 10)

Third Group:
(1) a probe having a base sequence comprising gatacagggccctttcgggtct;          (SEQ ID NO: 11)

(2) a probe having a base sequence comprising ttttggcgagtactggacccaac;         (SEQ ID NO: 12)

(3) a probe having a base sequence comprising ctaaccattcgccttgtggtgtt;         (SEQ ID NO: 13)

(4) a probe having a base sequence comprising atcgggtgttgttctttttttgacgc;      (SEQ ID NO: 14)

and
(5) a probe having a base sequence comprising aaatagtgctgctagcttttgctggt       (SEQ ID NO: 15)

Fourth Group:
(1) a probe having a base sequence comprising atataacgatacagggcctttggtcttg;    (SEQ ID NO: 16)

(2) a probe having a base sequence comprising ggcggacggtctacctatggtaa;         (SEQ ID NO: 17)

(3) a probe having a base sequence comprising accaggacgattactttgaggaaattaga;   (SEQ ID NO: 18)

(4) a probe having a base sequence comprising ggtggtgctactttgcccactc;          (SEQ ID NO: 19)

(5) a probe having a base sequence comprising agacttctcttgatcttacgggtggt;      (SEQ ID NO: 20)

and
(6) a probe having a base sequence comprising aaatagggctgcgagcatctgc           (SEQ ID NO: 21)

Fifth Group:
(1) a probe having a base sequence comprising gccggtccatctttttgatgcgta;        (SEQ ID NO: 22)

(2) a probe having a base sequence comprising tctggctagccttttggcgaac;          (SEQ ID NO: 23)

(3) a probe having a base sequence comprising tcagtattcagtagtcagaggcgaaattc;   (SEQ ID NO: 24)

(4) a probe having a base sequence comprising tgttgttcttttattgacgcaatcggc;     (SEQ ID NO: 25)

and
(5) a probe having a base sequence comprising tgctgctagcatttgctggtatagtc       (SEQ ID NO: 26)

Sixth Group:
(1) a probe having a base sequence comprising acaatacagggctcttttgggcc;         (SEQ ID NO: 27)

(2) a probe having a base sequence comprising ctggtggtcctgtatgctctttactg;      (SEQ ID NO: 28)

(3) a probe having a base sequence comprising ttgacggaagaccaacaactgcg;         (SEQ ID NO: 29)

(4) a probe having a base sequence comprising gatcggcccacgtcaatctctg;          (SEQ ID NO: 30)

and
(5) a probe having a base sequence comprising cggcgtctagtcgacggaagtt           (SEQ ID NO: 31)

Seventh Group:
(1) a probe having a base sequence comprising gaggaacggtctgccttacggta;    (SEQ ID NO: 32)

(2) a probe having a base sequence comprising ttcattgagtgtgcggtggaacc;    (SEQ ID NO: 33)

(3) a probe having a base sequence comprising cttagatttacggaagactaacaactgcg;    (SEQ ID NO: 34)

(4) a probe having a base sequence comprising tcggtccacgttattttctgactgga;    (SEQ ID NO: 35)

and
(5) a probe having a base sequence comprising ggactaacagcgtttagctgttggaa    (SEQ ID NO: 36)

Eighth Group:
(1) a probe having a base sequence comprising ttctggggaacctcatggcctt;    (SEQ ID NO: 37)

(2) a probe having a base sequence comprising atagggatagtcggggcgtca;    (SEQ ID NO: 38)

(3) a probe having a base sequence comprising aaagcattcgccaaggatgttttcattaa;    (SEQ ID NO: 39)

(4) a probe having a base sequence comprising cggtgtttctatgatgaccgctc;    (SEQ ID NO: 40)

and
(5) a probe having a base sequence comprising cttcttagggggactatcggctca    (SEQ ID NO: 41)

Ninth Group:
(1) a probe having a base sequence comprising ggggctcttttgggtctcgtaatt;    (SEQ ID NO: 42)

(2) a probe having a base sequence comprising ctggggaatctcatggccttcac;    (SEQ ID NO: 43)

(3) a probe having a base sequence comprising ggatagtcggggcgtcagtatt;    (SEQ ID NO: 44)

(4) a probe having a base sequence comprising gtgtttctattatgaccgttcggca;    (SEQ ID NO: 45)

and
(5) a probe having a base sequence comprising agacctcggcccttaaatagccc    (SEQ ID NO: 46)

Each of the above groups has at least five kinds of probes, and using at least one kind of probe from each of at least two group selected from the first to ninth group, a probe set can be formed. Therefore, a probe set of this embodiment may contain two kinds of probes at minimum and 46 kinds of probes at maximum.

Here, each group has the following detection function.
First group: detection for *Candida albicans*
Second group: detection for *Candida glabrata*
Third group: detection for *Candida guilliermondii*
Fourth group: detection for *Candida krusei*
Fifth group: detection for *Candida parapsilosis*
Sixth group: detection for *Cryptococcus neoformans*
Seventh group: detection for *Trichosporon beigelii*
Eighth group: detection for *Aspergillus fumigatus*
Ninth group: detection for *Aspergillus niger*

Sequences complementary to these probe sequences also have the same functions, and thus they are effective as probe sequences. Probes having these complementary sequences are also usable to form a probe set.

Namely, the probe set is constituted to:
(1) include a first probe belonging to a group selected from the above first to ninth groups, and a second probe belonging to a group that is selected from the above first to ninth groups and different from the group of the first probe; or
(2) include a third probe having a base sequence complementary to the first probe, and a fourth probe having a base sequence complementary to the second probe.

The probes for the respective microorganisms were designed from 18S rRNA gene such that they could have a very high specificity with respect to the corresponding microorganisms, and a sufficient hybridization sensitivity with no variation between the probe base sequences could be expected.

These oligonucleotide probes are designed such that a stable hybrid body is formed by hybridization reaction between a specimen and two or more kinds of probes bonded onto a carrier, and a satisfactory result can be obtained.

Further, a probe-immobilized carrier (for example, DNA chip) having a probe of the present invention for infectious etiologic microorganism detection immobilized thereon, can be obtained by supplying and immobilizing each probe constituting the probe set of the present embodiment on a predetermined location of the carrier. For supplying the probe to the carrier, various methods are usable. For example, the following method can be preferably used: a probe is prepared so as to be immobilized on a carrier by chemical bonding (covalent bond), and a liquid containing the probe is supplied to a predetermined location of the carrier by liquid discharging method (i.e. inkjet method). This enables less peeling off of the probe from the carrier, and also the sensitivity is enhanced as an additional effect. When a DNA chip is prepared by a stamping method called Stanford method, the chip has a drawback that the applied DNA easily peels off. Further, as a method for producing a DNA chip, a probe is disposed by DNA synthesis on the surface of a carrier. In the method of synthesizing the probe on the carrier, a synthesis amount of each probe sequence is different and thus the amounts of immobilized probes are considerably different depending on the immobilized region (spot) of each probe. When such variations exist in the amount of immobilized probe, reliable evaluation may not be made on detection results obtained using such carrier. From these viewpoints, the probe-immobilized carrier of the present invention is prepared using the above-mentioned inkjet method since it is preferred in the following points: a probe hardly peels off and is fixed on a carrier stably; and probe-immobilized carriers for highly sensitive and accurate detection are provided efficiently.

Hereinafter, preferable embodiments of the present invention will be descried in detail.

Specimens as examination targets used for the DNA chip of the probe-immobilized carrier of the present embodiment, include any specimen in which microorganism may be present, and for example, body fluids originated in animals such as human and livestock, including blood, spinal fluid, phlegm, stomach fluid, vaginal secreted material, and intraoral mucus, and excretion such as urine and feces. Further, all media which may be contaminated by microorganisms can also be examination targets, including food and water in the environment such as drink water and hot spring water, which may cause food poisoning or may be contaminated, filters of such as air cleaners. Animals and plants to be quarantined at the time of import and export may be examination targets as specimen.

When the above specimen can be used for reaction with a DNA chip with no treatment, it is reacted with the DNA chip and the result is analyzed. Further, when the specimen cannot be reacted with the DNA chip with no treatment, treatments such as extraction and purification of a target substance, depending on the necessary, are made on the specimen and the obtained sample is allowed to react with the DNA chip. For example, when a target nucleic acid is contained in a specimen, an extract fraction that is assumed to contain the target nucleic acid is prepared from the specimen and further treatments such as washing or dilution are conducted if necessary. Then, the prepared sample solution is allowed to react with the DNA chip. Moreover, when a target nucleic acid is contained in a specimen, various amplification treatments including PCR amplification treatment may be conducted to amplify the target nucleic acid, thereby obtaining a sample to be reacted with the DNA chip. Examples of such amplified nucleic acid sample include specimens prepared by various methods, such as an amplified specimen prepared by using PCR reaction primer designed for detecting 18S rRNA gene; a specimen prepared by conducting PCR reaction, etc. of a PCR-amplified product; a specimen prepared by an amplification method other than PCR; a specimen labeled by various labeling methods for visualization.

The carrier used for the DNA chip of this embodiment includes all sorts of carriers that satisfy the characteristic as the carrier including flat substrates such as a glass substrate, a plastic substrate, and a silicon wafer, a three-dimensional structure having a three-dimensional pattern, a spherical body such as a bead, and rod-, cord-, and thread-shaped structures. The carrier also includes a substrate whose surface is processed such that a probe DNA can be immobilized. Especially, a carrier prepared by introducing a functional group to its surface to make chemical reaction possible has a preferable form from the viewpoint of reproducibility because the probe is stably bonded in the process of hybridization reaction.

As an example of the immobilization method used in the present invention, a combination of a maleimide group and a thiol (—SH) group is used. More specifically, a thiol (—SH) group is bonded to the terminal of a nucleic acid probe, and the carrier surface (solid phase) is treated so as to have a maleimide group. Accordingly, the thiol group of the nucleic acid probe supplied to the solid surface reacts with the maleimide group on the solid surface to immobilize the nucleic acid probe.

To introduce the maleimide group, first, an aminosilane coupling agent is caused to react on a glass substrate. Next, the maleimide group is introduced by reaction between the amino group and an EMCS reagent (N-(6-Maleimidocaproyloxy)succinimide: manufactured by Dojin). Introduction of the SH group to a DNA can be done by using 5'-Thiol-ModifierC6 (manufactured by Glen Research) when the DNA is synthesized by an automatic DNA synthesizer.

Instead of the above-described combination of a thiol group and a maleimide group, a combination of, e.g., an epoxy group (on the solid phase) and an amino group (nucleic acid probe terminal) can also be used as a combination of functional groups to be used for immobilization. Surface treatments using various kinds of silane coupling agents are also effective. Oligonucleotide in which a functional group which can react with a functional group introduced by a silane coupling agent is introduced is used. A method of applying a resin having a functional group can also be used.

Detection of an infectious etiologic microorganism gene using the probe-immobilized carrier of the present invention, can be carried out by a method for detecting the infectious etiologic microorganism gene. The method comprises the steps of: reacting the probe-immobilized carrier having the above structure with a specimen; detecting a reaction between the probe on the probe-immobilized carrier and a nucleic acid in the specimen (for example, detecting the presence of the reaction); and when the reaction therebetween is detected, specifying a probe having the reaction with the nucleic acid in the specimen to identify the infectious etiologic microorganism gene contained in the specimen based on the base sequence of the probe.

As mentioned above, when a 18S rRNA gene sequence contained in the specimen is amplified by PCR and the resultant product is used as a sample to be reacted with the probe carrier, a primer set for detecting an infectious etiologic microorganism is usable. As the primer set, those containing the following oligonucleotides as primers are preferable.

(1) an oligonucleotide comprising a base sequence of 5' gccctatcaactttcgatggtaggatag 3'
(2) an oligonucleotide comprising a base sequence of 5' aatgctctatccccagcacgac 3'

EXAMPLES

Hereafter, the present invention will be described in detail by referring to examples using probes for an infectious etiologic microorganism for detecting fungi.

Example 1

In the following example, detection of microorganisms using 2 Step PCR method will be described.

<1. Preparation of Probe DNAs>

Nucleic acid sequences shown in Table 1 were designed and synthesized as probes to be used for detection of the *Candida albicans*. More specifically, the following probe base sequences were selected from the 18S rRNA gene of *Candida albicans*. These probe base sequences were designed such that they could have a very high specificity with respect to the corresponding fungus, and sufficient hybridization sensitivity with no variation between the probe base sequences could be expected. The probe base sequences to be used are not limited to ones completely agreeing with those shown in Table 1, but probe base sequences having base lengths of about 20 to 30 and including the probe base sequences are also included in the probe base sequence shown in Table 1.

TABLE 1

| Name of micro-organism | Probe No. | SEQ ID NO | Sequence |
|---|---|---|---|
| Candia albicans | CA-1 | 1 | 5' acgatacagggccctttttgggt 3' |
|  | CA-2 | 2 | 5' atcttttttcgatgcgtactggaccag 3' |
|  | CA-3 | 3 | 5' gccatttatggcgaaccaggactt 3' |
|  | CA-4 | 4 | 5' aggacgttatggttctattgtgttggtt 3' |
|  | CA-5 | 5 | 5' ggactatcgactccaagtcgatgga 3' |

For each probe shown in Table 1, as a functional group to immobilize the probe to a DNA microarray, a thiol group was introduced to the 5' terminal of the nucleic acid after synthesis in accordance with a conventional method. After introduction of the functional group, purification and freeze-drying were conducted. The freeze-dried probes for internal standards were stored in a freezer at −30° C.

<2. Preparation of PCR Primers>

<2-1. Preparation of Specimen Amplification PCR Primers>

As 18S rRNA gene (target gene) amplification PCR primers for etiologic microorganism detection, nucleic acid sequences shown in Table 2 were designed. More specifically, primer sets which specifically amplify the genome parts encoding the 18S rRNA genes, that is primers for which the specific melting points were made uniform as much as possible at the two end portions of the 18S rRNA gene coding region of a base length of about 1,700 were designed. In order to simultaneously amplify different strains of fungi, primers were designed from the common region among fungi.

TABLE 2

| Primer No. | SEQ ID NO | Sequence |
|---|---|---|
| Forward Primer F-1 | 47 | 5' gccctatcaactttcgatggtaggatag 3' |
| Reverse Primer R-1 | 48 | 5' aatgctctatccccagcacgac 3' |

The primers shown in Table 2 were purified by a high performance liquid chromatography (HPLC) after the synthesis, and each primer was dissolved in a TE buffer solution so as to have an ultimate concentration of 10 pmol/μl.

<2-2. Preparation of Labeling PCR Primers>

Primers for labeling were designed as shown in Table 3 in the same manner as specimen amplification primers mentioned above.

TABLE 3

| Primer No. | SEQ ID NO | Sequence |
|---|---|---|
| Cy3-labeled Primer R-2 | 49 | 5' tcggcaccttacgagaaatcaaagt 3' |

To the primers shown in Table 3, labeling was conducted using Cy3 as a fluorescent dye.

After the synthesis, the primer was purified by an HPLC, and the primer was dissolved in a TE buffer solution so as to have an ultimate concentration of 10 pmol/μl.

<3. Extraction of Genome DNAs (Model Specimens) of Candida albicans>

<3-1. Microbial Culture and Genome DNA Extraction>

First, a type strain of Candida albicans (ATCC 18804) was cultured in accordance with a conventional method. From the microbial culture solution, genome DNAs were extracted and purified using a nucleic acid purification kit (FastPrep FP100A·FastDNA Kit manufactured by Funakoshi Co., Ltd.).

<3-2. Test of Collected Genome DNAs>

On the collected genome DNAs of microorganism (Candida albicans), agarose electrophoresis and 260/280-nm absorbance determination were conducted in accordance with a conventional method so that the quality (contamination amount of low molecular nucleic acids and degradation degree) and collection amount were assayed. In this example, about 10 μg of genome DNAs was collected, and no degradation of genome DNAs and no contamination of rRNA were observed. The collected genome DNAs were dissolved in a TE buffer solution so as to have an ultimate concentration of 50 ng/μl, and used in the following examples.

<4. Preparation of DNA Microarray>

<4-1. Cleaning of Glass Substrate>

A glass substrate (size: 25 mm×75 mm×1 mm, manufactured by Iiyama Tokushu Glass) made of synthetic silica was placed in a heat- and alkali-resistant rack and soaked in a cleaning solution for ultrasonic cleaning, which was prepared to have a predetermined concentration. The glass substrate was kept soaked in the cleaning solution overnight and then cleaned for 20 min. by ultrasonic cleaning. The substrate was picked up, lightly rinsed by pure water, and cleaned for 20 min. by ultrasonic cleaning in ultrapure water. Next, the substrate was soaked in 1N aqueous sodium hydroxide solution heated to 80° C. for 10 min. Pure water cleaning and ultrapure water cleaning were conducted again. A silica glass substrate for a DNA chip was thus prepared.

<4-2. Surface Treatment>

A silane coupling agent KBM-603 (manufactured by Shinetsu Silicone) was dissolved in pure water at a concentration of 1% by weight and stirred at room temperature for 2 hours. Then, the cleaned glass substrate was dipped in the aqueous solution of the silane coupling agent and allowed to stand for 20 min. at room temperature. The glass substrate was pulled out. The surface thereof was lightly rinsed by pure water and dried by spraying nitrogen gas to both surfaces of the substrate. The dried substrate was baked in an oven at 120° C. for 1 hour to complete the coupling agent treatment, thereby introducing an amino group to the substrate surface. Next, N-(6-maleimidocaproyloxy)succinimido (hereafter abbreviated as EMCS) was dissolved in a solvent mixture of dimethyl sulfoxide and ethanol (volume ratio=1:1) so as to have an ultimate concentration of 0.3 mg/ml, thereby preparing an EMCS solution. EMCS was N-(6-Maleimidocaproyloxy)succinimido manufactured by Dojindo Laboratories.

The baked glass substrate was allowed to stand for cooling, and dipped in the prepared EMCS solution at room temperature for 2 hours. This treatment allows the amino group introduced to the surface by the silane coupling agent to react with the succinimide group in the EMCS, so that the maleimide group was introduced to the surface of the glass substrate. The glass substrate pulled out from the EMCS solution was cleaned by using the above-mentioned solvent mixture having EMCS dissolved therein. The glass substrate was further cleaned by ethanol and dried in an atmosphere of nitrogen gas.

<4-3. Probe DNA>

The microorganism detection probe prepared in <1. Preparation of Probe DNA> of Example 1 was dissolved in pure water. The solution was dispensed such that the ultimate concentration (at ink dissolution) became 10 μM. Then, the solution was freeze-dried to remove water.

<4-4. DNA Discharge by BJ Printer and Bonding to Substrate>

An aqueous solution containing 7.5 wt % of glycerin, 7.5 wt % of thiodiglycol, 7.5 wt % of urea, and 1.0 wt % of acetylenol EH (manufactured by Kawaken Fine Chemicals) was prepared. Each of 5 kinds of probes (Table 1) prepared in advance was dissolved in the above solvent mixture so as to have a normal concentration. The obtained DNA solution was packed into an ink tank of a bubble jet printer (tradename: BJF-850 manufactured by Canon), and the tank was attached to the printerhead.

The bubble jet printer used here was modified in advance to enable printing on a flat plate. Further, input of a printing pattern in accordance with a predetermined file creation method into this bubble jet printer enables about 5 picoliter of a DNA solution to be spotted at a pitch of about 120 μm.

Then, this modified bubble jet printer was used for printing operation on one glass substrate thereby to prepare an array. After confirming that the printing was reliably achieved, the glass substrate was allowed to stand in a humidified chamber for 30 min. to react the maleimide group on the glass substrate surface with the thiol group at the terminal of the nucleic acid probe.

<4-5. Washing>

After 30 minutes of reaction, the DNA solution remaining on the surface was washed by 10 mM phosphate buffer solution (pH 7.0) containing 100 mM NaCl, thereby obtaining a DNA microarray having single-stranded DNAs immobilized on the glass substrate surface.

<5. Amplification and Labeling of Specimens>
<5-1. Amplification of Specimens: 1st PCR>

Amplification (1st PCR) of microbial genes as specimens and labeling (2nd PCR) reaction will be shown below in Table 4.

TABLE 4

| | |
|---|---|
| AmpliTaq Gold (5 U/μL) | 0.5 μL |
| Template Genome DNA | Variable |
| dNTP mix (2.5 mM/each) | 4.0 μL |
| ×10 PCR buffer | 5.0 μL |
| 25 mM MgCl$_2$ | 7.0 μL |
| Forward Primer | 0.25 μL |
| Reverse Primer | 0.25 μL |
| H$_2$O | Variable |
| Total | 50 μl |

Amplification reaction of the reaction solution having the above composition was conducted by a commercially available thermal cycler in accordance with the protocol shown in FIG. 1.

After the end of reaction, purification was conducted using a purification column (QIAquick PCR Purification Kit manufactured by QIAGEN), and then amplified products were assayed.

<5-2. Labeling Reaction: 2nd PCR>

Amplification reaction of the reaction solution having the composition of Table 5 was conducted by a commercially available thermal cycler in accordance with the protocol shown in FIG. 2.

TABLE 5

| | |
|---|---|
| Premix PCR reagent (TAKARA ExTaq) | 25 μL |
| Template DNA (1st PCR Product) | Variable (30 ng/tube) |
| Cy3-labeled Reverse Primer | 5 μL |
| H$_2$O | Variable |
| Total | 50 μL |

After the end of reaction, purification was conducted using a purification column (QIAquick PCR Purification Kit manufactured by QIAGEN) to obtain labeled specimens.

<6. Hybridization>

Detection reaction was performed by using the DNA microarrays prepared in the above process <4. Preparation of DNA Microarray> and the labeled specimens prepared in the above process <5. Amplification and Labeling of Specimens>.

<6-1. Blocking of DNA Microarrays>

BSA (bovine serum albumin, Fraction V manufactured by Sigma) was dissolved in a 100-mM NaCl/10-mM phosphate buffer so as to have a concentration of 1 wt %. Next, the DNA microarrays prepared in the process <4. Preparation of DNA Microarrays> were dipped in the solution at room temperature for 2 hours for blocking. After the end of blocking, the chips were washed with the following washing solution, rinsed with pure water, and dehydrated by a spin dryer.

Washing Solution:

2×SSC solution (NaCl 300 mM, sodium citrate (trisodium citrate dehydrate, $C_6H_5Na_3.2H_2O$) 30 mM, pH 7.0) containing 0.1 wt % SDS (sodium dodecyl sulfate)

<6-2. Hybridization>

The dehydrated DNA microarrays were set in a hybridization apparatus (Hybridization Station manufactured by Genomic Solutions Inc.), and hybridization reaction was performed using a hybridization solution under the conditions shown below.

<6-3.> Hybridization Solution

6×SSPE/10% formamide/Target (all 2nd PCR products)/0.05 wt % SDS (6×SSPE: NaCl 900 mM, $NaH_2PO_4.H_2O$ 50 mM, EDTA 6 mM, pH 7.4)

<6-4. Hybridization Conditions>

65° C. 3 min.→92° C. 2 min.→45° C. 3 hrs→Wash 2×SSC/0.1% SDS at 25° C.→Wash 2×SSC at 20° C.→(Rinse with H$_2$O: Manual)→Spin dry.

<7. Microorganism Detection (Fluorometry)>

The DNA microarrays after the end of hybridization reaction were subjected to fluorometry using a DNA microarray fluorescent detector (GenePix 4000B manufactured by Axon). As a result, *Candida albicans* was detected by sufficient signal with high reproducibility. No definite hybrid bodies for probes from other microorganisms were not detected.

<8. Detection of Other Microorganisms>

Probe sets for detecting each microorganism listed below were designed and prepared, and examinations (hybridization reaction) were conducted in the same manner as described above. In Tables 6 to 14, sequences of probes used for the probe sets are shown by SEQ ID NOS.

(1) *Candida glabrata*

(2) *Candida guilliermondii*

(3) *Candida krusei*

(4) *Candida parapsilosis*

(5) *cryptococcus neoformans*

(6) *Trichosporon beigelii*

(7) *Aspergillus fumigatus*

(8) *Aspergillus niger*

<9. Results>

Results are shown in Table 6 to 14. In accordance with SN ratio of intensity values obtained from the experiments, the following signs are used. When the SN ratio is greater than 3, "+++" is used. For the SN ratio of greater than 2 and not greater than 3, greater than 1 and not greater than 2, and not greater than 1, "++", "+" and "−" are used, respectively.

TABLE 6

*Candida albicans*

| Name of microorganism | SEQ ID NO: 1 | SEQ ID NO: 2 | SEQ ID NO: 3 | SEQ ID NO: 4 | SEQ ID NO: 5 |
|---|---|---|---|---|---|
| Candida albicans | +++ | +++ | +++ | +++ | +++ |
| Candida glabrata | − | − | − | − | − |
| Candida guilliermondii | ++ | − | + | + | ++ |
| Candida krusei | ++ | − | + | + | − |
| Candida parapsilosis | ++ | ++ | ++ | ++ | ++ |
| Cryptococcus neoformans | − | − | − | − | − |
| Trichosporon beigelii | − | − | − | − | − |
| Aspergillus fumigatus | − | − | + | − | − |
| Aspergillus niger | − | − | + | − | − |
| Human 18S rRNA | − | − | − | − | − |

TABLE 7

*Candida glabrata*

| Name of microorganism | SEQ ID NO: 6 | SEQ ID NO: 7 | SEQ ID NO: 8 | SEQ ID NO: 9 | SEQ ID NO: 10 |
|---|---|---|---|---|---|
| Candida albicans | − | − | + | − | + |
| Candida glabrata | +++ | +++ | +++ | +++ | +++ |
| Candida guilliermondii | − | − | ++ | + | − |
| Candida krusei | − | − | − | + | − |
| Candida parapsilosis | − | − | ++ | − | + |
| Cryptococcus neoformans | − | − | − | − | − |
| Trichosporon beigelii | − | − | + | − | − |
| Aspergillus fumigatus | − | − | ++ | − | − |
| Aspergillus niger | − | − | ++ | − | − |
| Human 18S rRNA | − | − | − | − | − |

TABLE 8

*Candida guilliermondii*

| Name of microorganism | SEQ ID NO: 11 | SEQ ID NO: 12 | SEQ ID NO: 13 | SEQ ID NO: 14 | SEQ ID NO: 15 |
|---|---|---|---|---|---|
| Candida albicans | − | + | − | − | ++ |
| Candida glabrata | + | − | − | − | − |
| Candida guilliermondii | +++ | +++ | +++ | +++ | +++ |
| Candida krusei | + | − | − | − | − |
| Candida parapsilosis | +++ | + | − | − | ++ |
| Cryptococcus neoformans | − | − | − | − | − |
| Trichosporon beigelii | − | − | − | − | − |
| Aspergillus fumigatus | − | + | − | − | − |
| Aspergillus niger | − | + | − | − | − |
| Human 18S rRNA | − | − | − | − | − |

TABLE 9

*Candida krusei*

| Name of microorganism | SEQ ID NO: 16 | SEQ ID NO: 17 | SEQ ID NO: 18 | SEQ ID NO: 19 | SEQ ID NO: 20 | SEQ ID NO: 21 |
|---|---|---|---|---|---|---|
| Candida albicans | + | − | − | − | − | − |
| Candida glabrata | − | − | − | − | − | − |
| Candida guilliermondii | + | − | − | − | − | − |
| Candida krusei | +++ | +++ | +++ | +++ | +++ | +++ |
| Candida parapsilosis | + | − | − | − | − | − |
| Cryptococcus neoformans | − | − | − | − | − | − |
| Trichosporon beigelii | − | − | − | − | − | − |
| Aspergillus fumigatus | − | − | − | − | − | − |
| Aspergillus niger | − | − | − | − | − | − |
| Human 18S rRNA | − | − | − | − | − | − |

TABLE 10

*Candida parapsilosis*

| Name of microorganism | SEQ ID NO: 22 | SEQ ID NO: 23 | SEQ ID NO: 24 | SEQ ID NO: 25 | SEQ ID NO: 26 |
|---|---|---|---|---|---|
| Candida albicans | ++ | − | + | ++ | ++ |
| Candida glabrata | − | − | − | − | − |
| Candida guilliermondii | − | + | ++ | ++ | ++ |
| Candida krusei | − | + | ++ | − | − |
| Candida parapsilosis | +++ | +++ | +++ | +++ | +++ |
| Cryptococcus neoformans | − | − | − | − | − |
| Trichosporon beigelii | − | − | − | − | − |
| Aspergillus fumigatus | − | − | + | − | − |
| Aspergillus niger | − | − | + | − | − |
| Human 18S rRNA | − | − | − | − | − |

TABLE 11

Cryptococcus neoformans

| Name of microorganism | SEQ ID NO: 27 | SEQ ID NO: 28 | SEQ ID NO: 29 | SEQ ID NO: 30 | SEQ ID NO: 31 |
|---|---|---|---|---|---|
| Candida albicans | − | − | − | − | − |
| Candida glabrata | − | − | − | − | − |
| Candida guilliermondii | − | − | − | − | − |
| Candida krusei | − | − | − | − | − |
| Candida parapsilosis | − | − | − | − | − |
| Cryptococcus neoformans | +++ | +++ | +++ | +++ | +++ |
| Trichosporon beigelii | − | − | − | − | − |
| Aspergillus fumigatus | + | − | − | − | − |
| Aspergillus niger | + | − | − | − | − |
| Human 18S rRNA | − | − | − | − | − |

TABLE 12

Trichosporon beigelii

| Name of microorganism | SEQ ID NO: 32 | SEQ ID NO: 33 | SEQ ID NO: 34 | SEQ ID NO: 35 | SEQ ID NO: 36 |
|---|---|---|---|---|---|
| Candida albicans | − | − | − | − | − |
| Candida glabrata | − | − | − | − | − |
| Candida guilliermondii | − | − | ++ | − | − |
| Candida krusei | − | − | − | − | − |
| Candida parapsilosis | − | − | − | − | − |
| Cryptococcus neoformans | − | − | − | − | − |
| Trichosporon beigelii | +++ | +++ | +++ | +++ | +++ |
| Aspergillus fumigatus | − | − | − | − | − |
| Aspergillus niger | − | − | − | − | − |
| Human 18S rRNA | − | − | − | − | − |

TABLE 13

Aspergillus fumigatus

| Name of microorganism | SEQ ID NO: 37 | SEQ ID NO: 38 | SEQ ID NO: 39 | SEQ ID NO: 40 | SEQ ID NO: 41 |
|---|---|---|---|---|---|
| Candida albicans | − | − | + | − | − |
| Candida glabrata | − | − | ++ | − | + |
| Candida guilliermondii | − | − | ++ | − | − |
| Candida krusei | + | − | ++ | − | − |
| Candida parapsilosis | − | − | + | − | − |
| Cryptococcus neoformans | − | − | − | − | − |
| Trichosporon beigelii | − | − | − | − | − |
| Aspergillus fumigatus | +++ | +++ | +++ | +++ | +++ |
| Aspergillus niger | ++ | +++ | +++ | + | +++ |
| Human 18S rRNA | − | − | ++ | − | − |

TABLE 14

Aspergillus niger

| Name of microorganism | SEQ ID NO: 42 | SEQ ID NO: 43 | SEQ ID NO: 44 | SEQ ID NO: 45 | SEQ ID NO: 46 |
|---|---|---|---|---|---|
| Candida albicans | + | − | − | − | − |
| Candida glabrata | − | − | − | − | − |
| Candida guilliermondii | − | − | − | − | − |
| Candida krusei | − | + | − | − | − |
| Candida parapsilosis | − | − | − | − | − |
| Cryptococcus neoformans | + | − | − | − | − |
| Trichosporon beigelii | − | − | − | − | − |
| Aspergillus fumigatus | +++ | ++ | +++ | − | ++ |
| Aspergillus niger | +++ | +++ | +++ | +++ | +++ |
| Human 18S rRNA | − | − | − | − | − |

As described above, DNA microarrays were prepared, on which probe sets capable of detecting 9 species of microorganisms of Tables 6 to 14 were immobilized, in accordance with the above example. Further, use of this DNA microarray enables the identification of infectious etiologic microorganisms, thereby solving the problem on DNA probes derived from microorganisms. Namely, an oligonucleotide probe can be chemically synthesized in mass, and control of purification and concentration is possible. Further, with an object of classification by species of fungus, a probe set can be provided, which is capable of collectively detecting microorganisms of the same species while differentiating microorganisms of other species.

According to the above embodiment, 18S rRNA gene sequence of an infectious etiologic microorganism is detected without excess and deficiency, and thereby the presence of the infectious etiologic microorganism can be determined with good efficiency and high accuracy.

Further, as can be seen from the above example, two or more kinds of probes from the same group, preferably three or more, more preferably all the five kinds, for example, are used, and analysis of signal ratio relative to each signal obtained enables highly accurate determination.

Example 2

In Examples described hereinafter, amplification of 9 kinds of microorganisms used in Example 1 will be explained.

<1. Preparation of Specimen Amplification PCR Primers>

As 18S rRNA gene (target gene) amplification PCR primers for specimen amplification, nucleic acid sequences shown in Table 2 were designed.

More specifically, primer sets which specifically amplify the 18S rRNA genes, that is primers for which the specific melting points were made uniform as much as possible at the two end portions of the 18S rRNA gene coding region of a base length of about 1,700 were designed. The primers were designed so as to simultaneously amplify variant strains or a plurality of 18S rRNA gene coding regions present on the genome.

Further, even in an experimental system having particularly human genome and fungal genome mixed therein, the primers were designed so as to selectively amplify fungal genome only.

TABLE 15

| Primer | SEQ ID NO | Sequence |
|---|---|---|
| Forward Primer | F-1 | 47 5' gccctatcaactttcgatggtaggatag 3' |
| Reverse Primer | R-1 | 48 5' aatgctctatccccagcacgac 3' |
| | R-2 | 49 5' tcggcaccttacgagaaatcaaagt 3' |

The primers shown in Table 15 were purified by a high performance liquid chromatography (HPLC) after the synthesis, and Forward Primer and two kinds of Reverse Primers were all mixed with each other. At that time, they were dissolved in a TE buffer solution so that each primer had an ultimate concentration of 10 pmol/μl. In this example, two kinds of Reverse Primers were used, but any one of them may be used.

<2. Extraction of Genome DNAs (Model Specimens) of *Candida albicans*>

<2-1. Microbial Culture and Genome DNA Extraction>

First, a standard strain of *Candida albicans* (ATCC18804) was cultured in accordance with a conventional method. From the microbial culture solution, genome DNAs were extracted and purified using a nucleic acid purification kit (FastPrep FP100A·FastDNA Kit manufactured by Funakoshi Co., Ltd.).

<2-2. Test of Collected Genome DNAs>

On the collected genome DNAs of microorganism (*Candida albicans*), agarose electrophoresis and 260/280-nm absorbance determination were conducted in accordance with a conventional method so that the quality (contamination amount of low molecular nucleic acids and degradation degree) and collection amount were assayed. In this example, about 10 μg of genome DNAs was collected, and no degradation of genome DNAs and no contamination of rRNA were observed. The collected genome DNAs were dissolved in a TE buffer solution so as to have an ultimate concentration of 50 ng/μl, and used as shown below.

Using the above DNAs, a reaction solution shown in Table 16 was prepared.

TABLE 16

| | | |
|---|---|---|
| Premix PCR reagent (TAKARA ExTaq) | 25 μl | |
| Template Genome DNA | 2 μl | (100 ng) |
| Forward Primer | 2 μl | |
| Reverse Primer mix | 2 μl | (20 pmol/tube each) |
| Cy-3 dUTP | 2 μl | (2 nmol/tube) |
| H$_2$O | 17 μl | |
| Total | 50 μl | |

Amplification reaction of the reaction solution having the above composition was conducted by a commercially available thermal cycler in accordance with the protocol shown in FIG. 1. After the end of reaction, purification was conducted using a purification column (QIAquick PCR Purification Kit manufactured by QIAGEN), the amplified products were subjected to gel electrophoresis. As a result of that, one band was detected near 1700 base-pair region from all nine kinds of microorganisms, which confirmed that PCR reaction was well conducted.

Example 3

The following Example describes that a portion encoding 18S rRNA in human genome cannot be amplified by the primer used in Example 2.

As a template for PCR reaction, human genome was subjected to PCR reaction using the primer set in the same manner in Example 2. As a result, no band that was amplified by PCR was not detected, which confirmed that amplification of human genome cannot be conducted by the primer set of Table 15 in Example 2. This indicates that the primer set of the present invention can selectively amplify only a 18S rRNA gene of microorganism genome from a clinical specimen that may have human genome and fungal genome mixed therein.

Example 4

The following Example describes that when two microorganisms are included in a specimen, both microorganisms can be detected simultaneously.

<1. Preparation of Specimen Model>

In accordance with the method described in <3-1. Microbial culture and Genome DNA Extraction> of Example 1, *Candida krusei* and *Aspergillus fumigatus* were cultured, and extraction and purification of Genome DNA were conducted.

<2. Preparation of DNA Microarray>

In accordance with the method described in <4. Preparation of DNA Microarray> of Example 1, DNA microarrays were prepared. An object of this Example is that *Candida krusei* and *Aspergillus fumigatus* can be detected simultaneously, and thus DNA microarrays having only probes shown in Table 17 below immobilized thereon were prepared.

TABLE 17

| SEQ ID NO | Kind of target microorganism |
|---|---|
| SEQ ID NO: 5 | *Candida albicans* |
| SEQ ID NO: 6 | *Candida glabrata* |
| SEQ ID NO: 7 | |
| SEQ ID NO: 10 | |
| SEQ ID NO: 13 | *Candida guilliermondii* |
| SEQ ID NO: 14 | |
| SEQ ID NO: 17 | *Candida krusei* |
| SEQ ID NO: 18 | |
| SEQ ID NO: 19 | |
| SEQ ID NO: 22 | *Candida parapsilosis* |
| SEQ ID NO: 27 | *Cryptococcus neoformans* |
| SEQ ID NO: 28 | |
| SEQ ID NO: 32 | *Trichosporon beigelii* |
| SEQ ID NO: 33 | |
| SEQ ID NO: 39 | *Aspergillus fumigatus* |
| SEQ ID NO: 40 | |
| SEQ ID NO: 41 | |
| SEQ ID NO: 45 | *Aspergillus niger* |

<3. Amplification and Labeling of Specimen>

The Genome DNAs of *Candida krusei* and *Aspergillus fumigatus* extracted and purified in the process of <1. Preparation of Specimen Model> were mixed to obtain Template DNAs. The Template DNAs were amplified and labeled in accordance with the method described in <5. Amplification and Labeling of Specimens> of Example 1.

<4. Hybridization>

Detection reaction described in <6. Hybridization> of Example 1 was performed by using the labeled specimen prepared in the above-described <2. Amplification and Labeling of Specimen> and the DNA microarrays prepared in <4. Preparation of DNA Microarray> of Example 1.

<5. Microorganism Detection (Fluorescence Detection)>

The DNA microarrays after the above hybridization reaction were subjected to fluorometry using a DNA microarray fluorescent detector (GenePix 4000B manufactured by Axon). The same experiment was conducted twice, and the obtained intensities were standardized. The standardized results are shown below in Table 18.

In accordance with SN ratio of intensity values obtained from the examinations, the following signs are used. When the SN ratio is greater than 3, "+++" is used. For the SN ratio of greater than 2 and not greater than 3, greater than 1 and not greater than 2, and not greater than 1,"++", "+" and "−" are used, respectively.

TABLE 18

| SEQ ID NO | First experiment | Second experiment |
| --- | --- | --- |
| SEQ ID NO: 5 | ++ | ++ |
| SEQ ID NO: 6 | − | − |
| SEQ ID NO: 7 | − | − |
| SEQ ID NO: 10 | − | − |
| SEQ ID NO: 13 | − | − |
| SEQ ID NO: 14 | + | + |
| SEQ ID NO: 17 | +++ | +++ |
| SEQ ID NO: 18 | +++ | +++ |
| SEQ ID NO: 19 | +++ | +++ |
| SEQ ID NO: 22 | − | − |
| SEQ ID NO: 27 | − | − |
| SEQ ID NO: 28 | − | − |
| SEQ ID NO: 32 | − | − |
| SEQ ID NO: 33 | − | − |
| SEQ ID NO: 39 | +++ | +++ |
| SEQ ID NO: 40 | +++ | +++ |
| SEQ ID NO: 41 | +++ | +++ |

Although there were difference in absolute value of intensity between first and second experiments, it was found that, as a result of standardization, the intensities of SEQ ID NOS: 17, 18, 19, 39, 40 and 41 exhibited remarkably high intensities. Probes of these SEQ ID NOS are probes that determine *Candida krusei* and *Aspergillus fumigatus*, as shown in Table 17. In view of the above results, even though a specimen contains genomes of two kinds of microorganisms, the DNA chip of the present example can determine the presence of each microorganism.

The present invention is not limited to the above embodiments and various changes and modifications can be made within the spirit and scope of the present invention. Therefore to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2005-355977, filed Dec. 9, 2005, which is hereby incorporated by reference herein in its entirety.

What is claimed is:

1. A probe set for detecting an infectious etiologic microorganism gene, wherein the probe set includes a plurality of isolated and purified probes, the probe set comprising:

(1) a plurality of probes for specifically detecting a DNA of *Candida albicans* comprising each of the probes (1) to (5) from the following first group; and (2) a probe belonging to a group that is selected from the following second to ninth groups:

First group:
(1) a probe consisting of acgatacagggcccttttgggt (SEQ ID NO:1) or the complementary sequence thereof
(2) a probe consisting of atcttttcgatgcgtactggaccag (SEQ ID NO:2) or the complementary sequence thereof
(3) a probe consisting of gccatttatggcgaaccaggactt (SEQ ID NO:3) or the complementary sequence thereof
(4) a probe consisting of aggacgttatggttctattgtgttggtt (SEQ ID NO:4) or the complementary sequence thereof
(5) a probe consisting of ggactatcgactccaagtcgatgga (SEQ ID NO:5) or the complementary sequence thereof Second group:
(1) a probe consisting of cggtccgatttttcgtgtactgga (SEQ ID NO:6) or the complementary sequence thereof
(2) a probe consisting of aaccccaagtccttgtggcttg (SEQ ID NO:7) or the complementary sequence thereof
(3) a probe consisting of tggaataatggaataggacgtttggttct (SEQ ID NO:8) or the complementary sequence thereof
(4) a probe consisting of ttttagtgacccactcggcacct (SEQ ID NO:9) or the complementary sequence thereof
(5) a probe consisting of gctagcatttgctggttgtccact (SEQ ID NO:10) or the complementary sequence thereof
Third group:
(1) a probe consisting of gatacagggcccttcgggtct (SEQ ID NO:11) or the complementary sequence thereof
(2) a probe consisting of ttttggcgagtactggacccaac (SEQ ID NO:12) or the complementary sequence thereof
(3) a probe consisting of ctaaccattcgcccttgtggtgtt (SEQ ID NO:13) or the complementary sequence thereof
(4) a probe consisting of atcgggtgttgttcttttttgacgc (SEQ ID NO:14) or the complementary sequence thereof
(5) a probe consisting of aaatagtgctgctagcttttgctggt (SEQ ID NO:15) or the complementary sequence thereof
Fourth group:
(1) a probe consisting of atataacgatacagggcctttggtcttg (SEQ ID NO:16) or the complementary sequence thereof
(2) a probe consisting of ggcggacggtctacctatggtaa (SEQ ID NO:17) or the complementary sequence thereof
(3) a probe consisting of accaggacgattactttgaggaaattaga (SEQ ID NO:18) or the complementary sequence thereof
(4) a probe consisting of ggtggtgctactttgcccactc (SEQ ID NO:19) or the complementary sequence thereof
(5) a probe consisting of agacttctcttgatcttacgggtggt (SEQ ID NO:20) or the complementary sequence thereof
(6) a probe consisting of aaatagggctgcgagcatctgc (SEQ ID NO:21) or the complementary sequence thereof
Fifth group:
(1) a probe consisting of gccggtccatctttttgatgcgta (SEQ ID NO:22) or the complementary sequence thereof
(2) a probe consisting of tctggctagccttttggcgaac (SEQ ID NO:23) or the complementary sequence thereof
(3) a probe consisting of tcagtattcagtagtcagaggcgaaattc (SEQ ID NO:24) or the complementary sequence thereof
(4) a probe consisting of tgttgttcttttattgacgcaatcggc (SEQ ID NO:25) or the complementary sequence thereof
(5) a probe consisting of tgctgctagcatttgctggtatagtc (SEQ ID NO:26) or the complementary sequence thereof
Sixth group:
(1) a probe consisting of acaatacagggctcttttgggcc (SEQ ID NO:27) or the complementary sequence thereof
(2) a probe consisting of ctggtggtcctgtatgctcttactg (SEQ ID NO:28) or the complementary sequence thereof
(3) a probe consisting of ttgacggaagaccaacaactgcg (SEQ ID NO:29) or the complementary sequence thereof
(4) a probe consisting of gatcggcccacgtcaatctctg (SEQ ID NO:30) or the complementary sequence thereof
(5) a probe consisting of cggcgtctagtcgacggaagtt (SEQ ID NO:31) or the complementary sequence thereof
Seventh group:
(1) a probe consisting of gaggaacggtctgccttacggta (SEQ ID NO:32) or the complementary sequence thereof
(2) a probe consisting of ttcattgagtgtgcggtggaacc (SEQ ID NO:33) or the complementary sequence thereof
(3) a probe consisting of cttagatttacggaagactaacaactgcg (SEQ ID NO:34) or the complementary sequence thereof
(4) a probe consisting of tcggtccacgttattttctgactgga (SEQ ID NO:35) or the complementary sequence thereof
(5) a probe consisting of ggactaacagcgtttagctgttggaa (SEQ ID NO:36) or the complementary sequence thereof
Eighth group:
(1) a probe consisting of ttctggggaacctcatggcctt (SEQ ID NO:37) or the complementary sequence thereof
(2) a probe consisting of atagggatagtcgggggcgtca (SEQ ID NO:38) or the complementary sequence thereof
(3) a probe consisting of aaagcattcgccaaggatgttttcattaa (SEQ ID NO:39) or the complementary sequence thereof
(4) a probe consisting of cggtgtttctatgatgacccgctc (SEQ ID NO:40) or the complementary sequence thereof
(5) a probe consisting of cttcttaggggggactatcggctca (SEQ ID NO:41) or the complementary sequence thereof
Ninth group:
(1) a probe consisting of ggggctcttttgggtctcgtaatt (SEQ ID NO:42) or the complementary sequence thereof
(2) a probe consisting of ctggggaatctcatggccttcac (SEQ ID NO:43) or the complementary sequence thereof
(3) a probe consisting of ggatagtcgggggcgtcagtatt (SEQ ID NO:44) or the complementary sequence thereof
(4) a probe consisting of gtgtttctattatgacccgttcggca (SEQ ID NO:45) or the complementary sequence thereof
(5) a probe consisting of agacctcggcccttaaatagccc (SEQ ID NO:46) or the complementary sequence thereof.

2. A probe-immobilized carrier wherein a plurality of probes constituting the probe set of claim 1 are disposed on a solid phase carrier distantly from each other.

3. A method for detecting a nucleic acid of an infectious etiologic microorganism in a specimen using a probe-immobilized carrier, comprising the steps of:
(i) reacting the probe-immobilized carrier of claim 2 with the specimen;
(ii) detecting the reaction strength of a probe on the probe-immobilized carrier with a nucleic acid in the specimen; and
(iii) detecting the nucleic acid of the infectious etiologic microorganism based on the reaction strength between the probe on the probe-immobilized carrier and the nucleic acid in the specimen.

4. The method according to claim 3, further comprising the step of, before the step (i), amplifying nucleic acids present in the specimen using a primer set having a primer comprising the base sequence of gccctatcaactttcgatggtaggatag (SEQ ID NO:47) and at least one of the following primers:
(A) a primer comprising aatgctctatcccagcacgac (SEQ ID NO:48); and
(B) a primer comprising tcggcaccttacgagaaatcaaagt (SEQ ID NO:49).

5. A method for detecting an infectious etiologic microorganism in a sample comprising the steps of:
(i) amplifying nucleic acids present in a sample using a primer set comprising a primer comprising the base sequence of gccctatcaactttcgatggtaggatag (SEQ ID NO:47) and at least one of the following primers:
(A) a primer comprising aatgctctatcccagcacgac (SEQ ID NO:48); and
(B) a primer comprising tcggcaccttacgagaaatcaaagt (SEQ ID NO:49);
(ii) reacting the amplified nucleic acids of (i) with the probe-immobilized carrier of claim 2;

(iii) detecting the reaction strength of a probe on the probe-immobilized carrier with the amplified nucleic acids ; and (iv) detecting the infectious etiologic microorganism in the sample based on the reaction strength between the probe on the probe-immobilized carrier and the amplified nucleic acids.

6. A kit for detecting an infectious etiologic microorganism comprising the probe set of claim 1 and a primer set for in advance amplifying a nucleic acid in a specimen, said primer set having a primer comprising the base sequence of gccctatcaactttcgatggtaggatag (SEQ ID NO:47) and at least one of the following primers:

(1) a primer comprising aatgctctatccccagcacgac (SEQ ID NO:48); and (2) a primer comprising tcggcaccttacgagaaatcaaagt (SEQ ID NO:49).

7. A kit for detecting an infectious etiologic microorganism comprising the probe-immobilized carrier of claim 2 and a primer set for in advance amplifying a nucleic acid in a specimen, said primer set having a primer comprising the base sequence of gccctatcaactttcgatggtaggatag (SEQ ID NO:47) and at least one of the following primers:

(1) a primer comprising aatgctctatccccagcacgac (SEQ ID NO:48); and (2) a primer comprising tcggcaccttacgagaaatcaaagt (SEQ ID NO:49).

8. The probe set according to claim 1, comprising at least one probe from each of the second to ninth groups.

9. The probe set according to claim 1, comprising at least two probes from each of the second to ninth groups.

10. A probe set for detecting a DNA of *Candida albicans* which is a pathogenic fungus, comprising the following probes (A) to (E), wherein the probe set does not comprise another probe to detect *Candida albicans*:

(A) a probe consisting of acgatacagggccctttgggt (SEQ ID NO:1);

(B) a probe consisting of atcttttcgatgcgtactggaccag (SEQ ID NO:2);

(C) a probe consisting of gccatttatggcgaaccaggactt (SEQ ID NO:3);

(D) a probe consisting of aggacgttatggttctattgtgttggtt (SEQ ID NO:4); and (E) a probe consisting of ggactatcgactccaagtcgatgga (SEQ ID NO:5).

* * * * *

SEQUENCE LISTING

<160> NUMBER OF SEQ ID NOS: 49

<210> SEQ ID NO 1
<211> LENGTH: 22
<212> TYPE: DNA
<213> ORGANISM: Artificial
<220> FEATURE:
<223> OTHER INFORMATION: Probe for Candida albicans

<400> SEQUENCE: 1
acgatacagg gccctttttgg gt                                            22

<210> SEQ ID NO 2
<211> LENGTH: 26
<212> TYPE: DNA
<213> ORGANISM: Artificial
<220> FEATURE:
<223> OTHER INFORMATION: Probe for Candida albicans

<400> SEQUENCE: 2
atctttttcg atgcgtactg gaccag                                         26

<210> SEQ ID NO 3
<211> LENGTH: 24
<212> TYPE: DNA
<213> ORGANISM: Artificial
<220> FEATURE:
<223> OTHER INFORMATION: Probe for Candida albicans

<400> SEQUENCE: 3
gccatttatg gcgaaccagg actt                                           24

<210> SEQ ID NO 4
<211> LENGTH: 28
<212> TYPE: DNA
<213> ORGANISM: Artificial
<220> FEATURE:

<223> OTHER INFORMATION: Probe for Candida albicans

<400> SEQUENCE: 4
aggacgttat ggttctattg tgttggtt                28

<210> SEQ ID NO 5
<211> LENGTH: 25
<212> TYPE: DNA
<213> ORGANISM: Artificial
<220> FEATURE:
<223> OTHER INFORMATION: Probe for Candida albicans

<400> SEQUENCE: 5
ggactatcga ctccaagtcg atgga                25

<210> SEQ ID NO 6
<211> LENGTH: 25
<212> TYPE: DNA
<213> ORGANISM: Artificial
<220> FEATURE:
<223> OTHER INFORMATION: Probe for Candida glabrata

<400> SEQUENCE: 6
cggtccgatt ttttcgtgta ctgga                25

<210> SEQ ID NO 7
<211> LENGTH: 22
<212> TYPE: DNA
<213> ORGANISM: Artificial
<220> FEATURE:
<223> OTHER INFORMATION: Probe for Candida glabrata

<400> SEQUENCE: 7
aaccccaagt ccttgtggct tg                22

<210> SEQ ID NO 8
<211> LENGTH: 29
<212> TYPE: DNA
<213> ORGANISM: Artificial
<220> FEATURE:
<223> OTHER INFORMATION: Probe for Candida glabrata

<400> SEQUENCE: 8
tggaataatg gaataggacg tttggttct                29

<210> SEQ ID NO 9
<211> LENGTH: 23
<212> TYPE: DNA
<213> ORGANISM: Artificial
<220> FEATURE:
<223> OTHER INFORMATION: Probe for Candida glabrata

<400> SEQUENCE: 9
ttttagtgac ccactcggca cct                23

<210> SEQ ID NO 10
<211> LENGTH: 24
<212> TYPE: DNA
<213> ORGANISM: Artificial
<220> FEATURE:
<223> OTHER INFORMATION: Probe for Candida glabrata

<400> SEQUENCE: 10
gctagcattt gctggttgtc cact                24

<210> SEQ ID NO 11

```
<211> LENGTH: 22
<212> TYPE: DNA
<213> ORGANISM: Artificial
<220> FEATURE:
<223> OTHER INFORMATION: Probe for Candida guilliermondii

<400> SEQUENCE: 11
gatacagggc cctttcgggt ct                                                  22

<210> SEQ ID NO 12
<211> LENGTH: 23
<212> TYPE: DNA
<213> ORGANISM: Artificial
<220> FEATURE:
<223> OTHER INFORMATION: Probe for Candida guilliermondii

<400> SEQUENCE: 12
ttttggcgag tactggaccc aac                                                 23

<210> SEQ ID NO 13
<211> LENGTH: 24
<212> TYPE: DNA
<213> ORGANISM: Artificial
<220> FEATURE:
<223> OTHER INFORMATION: Probe for Candida guilliermondii

<400> SEQUENCE: 13
ctaaccattc gcccttgtgg tgtt                                                24

<210> SEQ ID NO 14
<211> LENGTH: 26
<212> TYPE: DNA
<213> ORGANISM: Artificial
<220> FEATURE:
<223> OTHER INFORMATION: Probe for Candida guilliermondii

<400> SEQUENCE: 14
atcgggtgtt gttctttttt tgacgc                                              26

<210> SEQ ID NO 15
<211> LENGTH: 26
<212> TYPE: DNA
<213> ORGANISM: Artificial
<220> FEATURE:
<223> OTHER INFORMATION: Probe for Candida guilliermondii

<400> SEQUENCE: 15
aaatagtgct gctagctttt gctggt                                              26

<210> SEQ ID NO 16
<211> LENGTH: 28
<212> TYPE: DNA
<213> ORGANISM: Artificial
<220> FEATURE:
<223> OTHER INFORMATION: Probe for Candida krusei

<400> SEQUENCE: 16
atataacgat acagggcctt tggtcttg                                            28

<210> SEQ ID NO 17
<211> LENGTH: 23
<212> TYPE: DNA
<213> ORGANISM: Artificial
<220> FEATURE:
<223> OTHER INFORMATION: Probe for Candida krusei

<400> SEQUENCE: 17
```

```
ggcggacggt ctacctatgg taa                                              23

<210> SEQ ID NO 18
<211> LENGTH: 29
<212> TYPE: DNA
<213> ORGANISM: Artificial
<220> FEATURE:
<223> OTHER INFORMATION: Probe for Candida krusei

<400> SEQUENCE: 18
accaggacga ttactttgag gaaattaga                                         29

<210> SEQ ID NO 19
<211> LENGTH: 22
<212> TYPE: DNA
<213> ORGANISM: Artificial
<220> FEATURE:
<223> OTHER INFORMATION: Probe for Candida krusei

<400> SEQUENCE: 19
ggtggtgcta ctttgcccac tc                                                22

<210> SEQ ID NO 20
<211> LENGTH: 26
<212> TYPE: DNA
<213> ORGANISM: Artificial
<220> FEATURE:
<223> OTHER INFORMATION: Probe  for Candida krusei

<400> SEQUENCE: 20
agacttctct tgatcttacg ggtggt                                            26

<210> SEQ ID NO 21
<211> LENGTH: 22
<212> TYPE: DNA
<213> ORGANISM: Artificial
<220> FEATURE:
<223> OTHER INFORMATION: Probe for Candida krusei

<400> SEQUENCE: 21
aaatagggct gcgagcatct gc                                                22

<210> SEQ ID NO 22
<211> LENGTH: 25
<212> TYPE: DNA
<213> ORGANISM: Artificial
<220> FEATURE:
<223> OTHER INFORMATION: Probe for Cryptococcus neoformans

<400> SEQUENCE: 22
gccggtccat cttttttgat gcgta                                             25

<210> SEQ ID NO 23
<211> LENGTH: 23
<212> TYPE: DNA
<213> ORGANISM: Artificial
<220> FEATURE:
<223> OTHER INFORMATION: Probe for Cryptococcus neoformans

<400> SEQUENCE: 23
tctggctagc cttttggcg aac                                                23

<210> SEQ ID NO 24
<211> LENGTH: 29
<212> TYPE: DNA
<213> ORGANISM: Artificial
<220> FEATURE:
```

<223> OTHER INFORMATION: Probe for Cryptococcus neoformans

<400> SEQUENCE: 24
tcagtattca gtagtcagag gcgaaattc                                29

<210> SEQ ID NO 25
<211> LENGTH: 27
<212> TYPE: DNA
<213> ORGANISM: Artificial
<220> FEATURE:
<223> OTHER INFORMATION: Probe for Cryptococcus neoformans

<400> SEQUENCE: 25
tgttgttctt ttattgacgc aatcggc                                  27

<210> SEQ ID NO 26
<211> LENGTH: 26
<212> TYPE: DNA
<213> ORGANISM: Artificial
<220> FEATURE:
<223> OTHER INFORMATION: Probe for Cryptococcus neoformans

<400> SEQUENCE: 26
tgctgctagc atttgctggt atagtc                                   26

<210> SEQ ID NO 27
<211> LENGTH: 23
<212> TYPE: DNA
<213> ORGANISM: Artificial
<220> FEATURE:
<223> OTHER INFORMATION: Probe for Cryptococcus neoformans

<400> SEQUENCE: 27
acaatacagg gctcttttgg gcc                                      23

<210> SEQ ID NO 28
<211> LENGTH: 26
<212> TYPE: DNA
<213> ORGANISM: Artificial
<220> FEATURE:
<223> OTHER INFORMATION: Probe for Cryptococcus neoformans

<400> SEQUENCE: 28
ctggtggtcc tgtatgctct ttactg                                   26

<210> SEQ ID NO 29
<211> LENGTH: 23
<212> TYPE: DNA
<213> ORGANISM: Artificial
<220> FEATURE:
<223> OTHER INFORMATION: Probe for Cryptococcus neoformans

<400> SEQUENCE: 29
ttgacggaag accaacaact gcg                                      23

<210> SEQ ID NO 30
<211> LENGTH: 22
<212> TYPE: DNA
<213> ORGANISM: Artificial
<220> FEATURE:
<223> OTHER INFORMATION: Probe for Cryptococcus neoformans

<400> SEQUENCE: 30
gatcggccca cgtcaatctc tg                                       22

<210> SEQ ID NO 31

```
<211> LENGTH: 22
<212> TYPE: DNA
<213> ORGANISM: Artificial
<220> FEATURE:
<223> OTHER INFORMATION: Probe for Cryptococcus neoformans

<400> SEQUENCE: 31
cggcgtctag tcgacggaag tt                                             22

<210> SEQ ID NO 32
<211> LENGTH: 23
<212> TYPE: DNA
<213> ORGANISM: Artificial
<220> FEATURE:
<223> OTHER INFORMATION: Probe for Trichosporon beigelii

<400> SEQUENCE: 32
gaggaacggt ctgccttacg gta                                            23

<210> SEQ ID NO 33
<211> LENGTH: 23
<212> TYPE: DNA
<213> ORGANISM: Artificial
<220> FEATURE:
<223> OTHER INFORMATION: Probe for Trichosporon beigelii

<400> SEQUENCE: 33
ttcattgagt gtgcggtgga acc                                            23

<210> SEQ ID NO 34
<211> LENGTH: 29
<212> TYPE: DNA
<213> ORGANISM: Artificial
<220> FEATURE:
<223> OTHER INFORMATION: Primer for PCR

<400> SEQUENCE: 34
cttagattta cggaagacta acaactgcg                                      29

<210> SEQ ID NO 35
<211> LENGTH: 26
<212> TYPE: DNA
<213> ORGANISM: Artificial
<220> FEATURE:
<223> OTHER INFORMATION: Probe for Trichosporon beigelii

<400> SEQUENCE: 35
tcggtccacg ttattttctg actgga                                         26

<210> SEQ ID NO 36
<211> LENGTH: 26
<212> TYPE: DNA
<213> ORGANISM: Artificial
<220> FEATURE:
<223> OTHER INFORMATION: Probe for Trichosporon beigelii

<400> SEQUENCE: 36
ggactaacag cgtttagctg ttggaa                                         26

<210> SEQ ID NO 37
<211> LENGTH: 22
<212> TYPE: DNA
<213> ORGANISM: Artificial
<220> FEATURE:
<223> OTHER INFORMATION: Probe for Aspergillus fumigatus

<400> SEQUENCE: 37
```
ttctggggaa cctcatggcc tt                                              22

<210> SEQ ID NO 38
<211> LENGTH: 22
<212> TYPE: DNA
<213> ORGANISM: Artificial
<220> FEATURE:
<223> OTHER INFORMATION: Probe for Aspergillus fumigatus

<400> SEQUENCE: 38
atagggatag tcggggcgt ca                                               22

<210> SEQ ID NO 39
<211> LENGTH: 29
<212> TYPE: DNA
<213> ORGANISM: Artificial
<220> FEATURE:
<223> OTHER INFORMATION: Probe for Aspergillus fumigatus

<400> SEQUENCE: 39
aaagcattcg ccaaggatgt tttcattaa                                       29

<210> SEQ ID NO 40
<211> LENGTH: 24
<212> TYPE: DNA
<213> ORGANISM: Artificial
<220> FEATURE:
<223> OTHER INFORMATION: Probe for Aspergillus fumigatus

<400> SEQUENCE: 40
cggtgtttct atgatgaccc gctc                                            24

<210> SEQ ID NO 41
<211> LENGTH: 24
<212> TYPE: DNA
<213> ORGANISM: Artificial
<220> FEATURE:
<223> OTHER INFORMATION: Probe for Aspergillus fumigatus

<400> SEQUENCE: 41
cttcttaggg ggactatcgg ctca                                            24

<210> SEQ ID NO 42
<211> LENGTH: 24
<212> TYPE: DNA
<213> ORGANISM: Artificial
<220> FEATURE:
<223> OTHER INFORMATION: Probe for Aspergillus niger

<400> SEQUENCE: 42
ggggctcttt tgggtctcgt aatt                                            24

<210> SEQ ID NO 43
<211> LENGTH: 23
<212> TYPE: DNA
<213> ORGANISM: Artificial
<220> FEATURE:
<223> OTHER INFORMATION: Probe for Aspergillus niger

<400> SEQUENCE: 43
ctggggaatc tcatggcctt cac                                             23

<210> SEQ ID NO 44
<211> LENGTH: 23
<212> TYPE: DNA
<213> ORGANISM: Artificial
<220> FEATURE:

```
<223> OTHER INFORMATION: Probe for Aspergillus niger

<400> SEQUENCE: 44
ggatagtcgg gggcgtcagt att                                          23

<210> SEQ ID NO 45
<211> LENGTH: 26
<212> TYPE: DNA
<213> ORGANISM: Artificial
<220> FEATURE:
<223> OTHER INFORMATION: Probe for Aspergillus niger

<400> SEQUENCE: 45
gtgtttctat tatgacccgt tcggca                                       26

<210> SEQ ID NO 46
<211> LENGTH: 23
<212> TYPE: DNA
<213> ORGANISM: Artificial
<220> FEATURE:
<223> OTHER INFORMATION: Probe for Aspergillus niger

<400> SEQUENCE: 46
agacctcggc ccttaaatag ccc                                          23

<210> SEQ ID NO 47
<211> LENGTH: 28
<212> TYPE: DNA
<213> ORGANISM: Artificial
<220> FEATURE:
<223> OTHER INFORMATION: Primer for PCR

<400> SEQUENCE: 47
gccctatcaa ctttcgatgg taggatag                                     28

<210> SEQ ID NO 48
<211> LENGTH: 22
<212> TYPE: DNA
<213> ORGANISM: Artificial
<220> FEATURE:
<223> OTHER INFORMATION: Primer for PCR

<400> SEQUENCE: 48
aatgctctat ccccagcacg ac                                           22

<210> SEQ ID NO 49
<211> LENGTH: 25
<212> TYPE: DNA
<213> ORGANISM: Artificial
<220> FEATURE:
<223> OTHER INFORMATION: Primer for PCR

<400> SEQUENCE: 49
tcggcacctt acgagaaatc aaagt                                        25
```